United States Patent [19]

Bergen

[11] 3,956,827
[45] May 18, 1976

[54] COLOR DISCRIMINATION TEST APPARATUS AND METHOD

[76] Inventor: Stephen Franklin Bergen, 1 Colonial Woods Drive, West Orange, N.J. 07052

[22] Filed: Dec. 12, 1974

[21] Appl. No.: 532,043

[52] U.S. Cl. .................................. 32/71; 35/28.3
[51] Int. Cl.² ........................................ A61C 19/00
[58] Field of Search ............... 32/71; 35/28.3, 28.5, 35/9 R

[56] References Cited
UNITED STATES PATENTS

| | | | |
|---|---|---|---|
| 2,805,478 | 9/1957 | Adams | 32/71 |
| 2,866,277 | 12/1958 | Wise | 35/28.3 |
| 3,474,546 | 10/1969 | Wedlake | 35/28.3 |
| 3,690,671 | 9/1972 | Slutsky | 35/28.3 |

*Primary Examiner*—Louis G. Mancene
*Assistant Examiner*—Jack Q. Lever
*Attorney, Agent, or Firm*—Charles I. Brodsky

[57] ABSTRACT

A color matching system, defined by "hue", "value" and "chroma" characteristics, is employed in a teaching program to develop an understanding of shade guide techniques for use by the dental profession.

3 Claims, 3 Drawing Figures

| | A | B | C | D | E |
|---|---|---|---|---|---|
| 1 | 11 | 51 | 12 | 52 | 21 |
| 2 | 42 | 3 | 43 | 13 | 61 |
| 3 | 2 | 73 | 10 | 53 | 22 |
| 4 | 41 | 33 | 63 | 23 | 62 |
| 5 | 1 | 72 | 32 | 71 | 31 |

Fig. 1.

|   | A | B | C | D | E |
|---|---|---|---|---|---|
| 1 | 11 | 51 | 12 | 52 | 21 |
| 2 | 42 | 3 | 43 | 13 | 61 |
| 3 | 2 | 73 | 10 | 53 | 22 |
| 4 | 41 | 33 | 63 | 23 | 62 |
| 5 | 1 | 72 | 32 | 71 | 31 |

Fig. 2.

|   | A | B | C | D | E |
|---|---|---|---|---|---|
| 1 | 14 | 54 | 15 | 55 | 24 |
| 2 | 45 | 6 | 46 | 16 | 64 |
| 3 | 5 | 20 | 30 | 56 | 25 |
| 4 | 44 | 36 | 66 | 26 | 65 |
| 5 | 4 | 75 | 35 | 74 | 34 |

Fig. 3.

|   | A | B | C | D | E |
|---|---|---|---|---|---|
| 1 | 17 | 57 | 28 | 68 | 27 |
| 2 | 58 | 29 | 69 | 39 | 67 |
| 3 | 18 | 60 | 70 | 40 | 38 |
| 4 | 47 | 59 | 50 | 49 | 9 |
| 5 | 7 | 19 | 48 | 8 | 37 |

COLOR DISCRIMINATION TEST APPARATUS AND METHOD

FIELD OF THE INVENTION

This invention relates to color discrimination test apparatus and, more particularly, to a teaching program for the improvement of shade guide techniques in the dental matching teeth.

BACKGROUND OF THE INVENTION

As is well understood, shade guides presently used by the dentist in matching teeth colors commonly employ 12–13 tooth samples. In use, the dentist holds this guide near a patient's mouth, in order to determine a correct shading for the face of a tooth to be crowned, or for the teeth of a denture, for example. While shade guides have been available for many years, they all generally suffer the same disadvantage in that the tooth samples are made of a porcelain type material which does not strictly conform to the tooth enamel; under different lighting conditions, it has been found that what once may have been a shading match, no longer continues. In addition, adjacent tooth samples oftentimes have no relationship, one to another, and exhibit large differences in shadings between them. When it is further realized that different manufacturers make their own shade guides, without there being any standardizations for shading in the profession, it will be apparent that the present day use of shade guides requires the giving of instructions to the laboratory to make a tooth facing "a little grayer" than sample No. 1, "a little yellower" than sample No. 2, etc. This also follows from the fact that the tooth samples represent what, over the course of years, have come to be accepted as "average" teeth, i.e., shades most often found in a patient's mouth.

It will thus be seen that while shade guides of these natures have found wide use, there still remains a need for improved shade guides and for improved techniques in their employment. However, it will be readily appreciated that before shade guides 50, 75, 100 or more tooth samples can be effectively used, the dentist must be taught to discern shading differences between a tooth sample and the tooth to which a comparison is then being made and, correspondingly, to determine when a shading match occurs.

SUMMARY OF THE INVENTION

As will become clear hereinafter, the color discrimination test apparatus of the present invention employs a color matching system, defined by hue, value and chroma characteristics. As herein utilized, hue represents the tint or color of a tooth, value represents the degree of its lightness or darkness, and chroma represents the extent of its color saturation. In a specific embodiment of the invention, some 75 samples of hue, value and chroma combinations are provided, within the ranges usually found in tooth enamels. It will be seen that some of the samples have corresponding hue, some have corresponding value, and some have corresponding chroma characteristics. As an aid in transferring the educational teachings which follow from the use of the program to be described to an actual operatory condition, those differences which are selected to exist between hues, values or chromas are selected to be within the perceptable range, but yet not so far apart that fine degrees of color matching or distinguishing can not be made.

In addition to providing the samples for use in analyzing colors and their characteristics within the dental range, a teaching program is described which has been found successful in improving the ability to detect differences between randomly selected samples. With such improved recognition of color characteristics, more advanced shade guides can be developed and made available for the better matching of teeth.

BRIEF DESCRIPTION OF THE DRAWING

These and other features of the present invention will be more clearly understood from a consideration of the following description taken in connection with the accompanying drawing in which:

FIGS. 1, 2 and 3 show locations of sample positionings in an array which are helpful in understanding the invention.

DETAILED DESCRIPTION OF THE DRAWING

I have found that the Munsell color matching system of hue, value and chroma can be used to teach dentists to distinguish, and match, tooth shading characteristics. Although it has been determined that differences in hue of 0.5 can be detected by the human eye, that differences in value of 0.1 can be detected, and that differences in chroma of 0.2 can be seen (these numbers, as employed in the Munsell system), I have selected the use of 75 color samples having characteristics which may vary slightly from these in attempting to strike a balance between the manufacturing costs involved, and the advantages to be gained with a large number of samples in the teaching program to be described. It has additionally been found that the dental range for hue in this Munsell system extends from approximately "7, yellowred" to approximately "4, yellow" (hues, generally, in the Munsell system, range from a number of 1 to 10, for each family of 10 colors). It has also been determined that lightness for teeth vary between 5 and 8.5 on the Munsell scale. It has additionally been found that a Munsell chroma range of 1.5 to 6.0 adequately covers most degrees of saturation that would be expected for tooth enamels.

With this in mind, I have devised a teaching system employing these 75 color samples, each of which is defined by a given hue, value and chroma characteristic within this dental range. It will readily be seen that use of dental colors in the training program simplifies the transition from the educational process in the classroom to the actual usage in the operatory. The table shown below defines each of the 75 color samples by number, with the column headed by the letter "V" representing the lightness or value of the sample, the column headed by the letter "H" representing its yellowish color or hue, and the column headed by the letter "C" representing its saturation or chroma. In devising this table, proposed quantities for the lightness or value characteristic were selected, but in the manufacture of the samples, the vagaries of the paints and papers employed — together with the intangibles of the printing processes followed — sometimes caused the sample to exhibit a value different from what was proposed. However, it will be understood that 3 separate values were selected for the 75 samples (namely 7.5, 7.75 and 8.0), and the hue and chroma levels were then varied amongst these 3 values.

The array of FIG. 1 shows the locations in a grid pattern of those samples having a common value of 7.5 (nominal). The array of FIGS. 2 and 3, similarly, show the locations of those samples having common values of 7.75 (nominal) and 8.0, respectively. Furthermore, samples within any column of each 8.0, (e.g. Column "A") exhibit chroma characteristics which increase from top to bottom (from line 1 through line 5). Additionally, the hue characteristic for each sample increases from left to right within any line (from Column "A" through Column "E").

In one use of the teaching program, the student would be asked to assemble these arrays based upon his observations of corresponding lightness characteristics, ascending saturation levels and increasing colors, in an attempt to duplicate the arrangements of FIGS. 1–3. As will be seen from FIGS. 1–3, the 75 samples are randomly numbered so as not to give any clues to their arrangement. However, as an aid to the instructor, it will be seen that samples properly belonging in the FIG. 1 array must either end in 1, 2 or 3, or must be the number 10. Similarly, only those samples which end in 4, 5, 6, or the numbers 20 and 30 should appear in the FIG. 2 grid pattern. Likewise, in reconstructing the array for FIG. 3, only those samples properly belong which end in 7, 8 or 9, or are the numbers 40, 50, 60 and 70. The degree of skill which the student gains through the teaching program can be rapidly determined by reviewing his assemblage of these arrangements.

There follows the identifying characteristics for each of the 75 samples employed in the teaching program.

The student, on this master definition sheet, could also be told that sample 29 is lighter than sample 3. (From the table, it will be seen that these two samples have substantially the same hue, 1.23Y, and chroma, 2.97, but a perceptibly different value, 8.0 as compared to 7.56.) Similarly, the student could be told that sample 35 is more saturated than sample 15. (From the table, it will be seen that the values and hues are identical, at 7.75 and 1.8Y, respectively, but the chromas are perceptibly different, 3.5 as compared to 2.83.) Lastly, the student could be told that sample 17 is less saturated than sample 7. (From the table, it will be seen that the values and hues are again identical, at 8.0 and 0.7Y, respectively, but the chromas are again different, 2.8 as compared to 3.5.) Here, too, it will be seen that samples are used whose characteristic differences are above the perceivable minimum, 0.1 for value, 0.5 for hue and 0.2 for chroma. During the course of working with these colors, the student could, if need be, refer to this definition sheet to review the kind of questions being asked.

In carrying out the teaching program, I have used 12 questions which I have found not only to be understandable by the student but to be a useful aid in teaching him to distinguish between colors. These questions and the methods of their usage will be apparent from the following description.

1. Question: Sample A is the same color as: (a) Sample 3; (b) Sample 13; (c) Sample 42; (d) Sample 43;

| No. | FIG. | V | H | C | No. | FIG. | V | H | C | No. | FIG. | V | H | C |
| --- | --- | --- | --- | --- | --- | --- | --- | --- | --- | --- | --- | --- | --- | --- |
| 1 | 1 | 7.51 | .25Y | 3.7 | 26 | 2 | 7.75 | 2.54Y | 3.3 | 51 | 1 | 7.57 | 1.42Y | 2.87 |
| 2 | 1 | 7.54 | .50Y | 3.3 | 27 | 3 | 8.0 | 2.7Y | 2.8 | 52 | 1 | 7.54 | 2.77Y | 2.83 |
| 3 | 1 | 7.56 | 1.32Y | 3.08 | 28 | 3 | 8.0 | 1.72Y | 2.8 | 53 | 1 | 7.56 | 2.71Y | 3.26 |
| 4 | 2 | 7.77 | .2Y | 3.5 | 29 | 3 | 8.0 | 1.23Y | 2.97 | 54 | 2 | 7.75 | 1.25Y | 2.84 |
| 5 | 2 | 7.75 | .45Y | 3.17 | 30 | 2 | 7.75 | 1.80Y | 3.2 | 55 | 2 | 7.75 | 2.35Y | 2.82 |
| 6 | 2 | 7.75 | 1.18Y | 3.0 | 31 | 1 | 7.54 | 3.45Y | 3.7 | 56 | 2 | 7.75 | 2.47Y | 3.2 |
| 7 | 3 | 8.0 | .7Y | 3.5 | 32 | 1 | 7.55 | 1.85Y | 3.7 | 57 | 3 | 8.0 | 1.23Y | 2.8 |
| 8 | 3 | 8.0 | 2.21Y | 3.5 | 33 | 1 | 7.53 | 1.14Y | 3.49 | 58 | 3 | 8.0 | .7Y | 2.97 |
| 9 | 3 | 8.0 | 2.7Y | 3.32 | 34 | 2 | 7.77 | 3.4Y | 3.6 | 59 | 3 | 8.0 | 1.23Y | 3.32 |
| 10 | 1 | 7.55 | 1.97Y | 3.27 | 35 | 2 | 7.75 | 1.8Y | 3.5 | 60 | 3 | 8.0 | 1.23Y | 3.15 |
| 11 | 1 | 7.58 | .75Y | 2.9 | 36 | 2 | 7.75 | 1.10Y | 3.33 | 61 | 1 | 7.54 | 3.45Y | 3.02 |
| 12 | 1 | 7.56 | 2.1Y | 2.85 | 37 | 3 | 8.0 | 2.7Y | 3.5 | 62 | 1 | 7.57 | 3.45Y | 3.47 |
| 13 | 1 | 7.54 | 2.74Y | 3.04 | 38 | 3 | 8.0 | 2.7Y | 3.15 | 63 | 1 | 7.55 | 1.91Y | 3.48 |
| 14 | 2 | 7.77 | .7Y | 2.85 | 39 | 3 | 8.0 | 2.21Y | 2.97 | 64 | 2 | 7.75 | 3.02Y | 3.0 |
| 15 | 2 | 7.75 | 1.8Y | 2.83 | 40 | 3 | 8.0 | 2.21Y | 3.15 | 65 | 2 | 7.75 | 3.27Y | 3.4 |
| 16 | 2 | 7.75 | 2.40Y | 3.0 | 41 | 1 | 7.52 | .37Y | 3.5 | 66 | 2 | 7.75 | 1.83Y | 3.3 |
| 17 | 3 | 8.0 | .7Y | 2.8 | 42 | 1 | 7.56 | .62Y | 3.1 | 67 | 3 | 8.0 | 2.7Y | 2.97 |
| 18 | 3 | 8.0 | .7Y | 3.15 | 43 | 1 | 7.55 | 2.03Y | 3.06 | 68 | 3 | 8.0 | 2.21Y | 2.8 |
| 19 | 3 | 8.0 | 1.23Y | 3.5 | 44 | 2 | 7.75 | .37Y | 3.33 | 69 | 3 | 8.0 | 1.72Y | 2.97 |
| 20 | 2 | 7.75 | 1.13Y | 3.17 | 45 | 2 | 7.75 | .57Y | 3.0 | 70 | 3 | 8.0 | 1.72Y | 3.15 |
| 21 | 1 | 7.53 | 3.45Y | 2.8 | 46 | 2 | 7.75 | 1.79Y | 3.0 | 71 | 1 | 7.57 | 2.65Y | 3.7 |
| 22 | 1 | 7.56 | 3.45Y | 3.25 | 47 | 3 | 8.0 | .7Y | 3.32 | 72 | 1 | 7.53 | 1.05Y | 3.7 |
| 23 | 1 | 7.56 | 2.68Y | 3.47 | 48 | 3 | 8.0 | 1.72Y | 3.5 | 73 | 1 | 7.54 | 1.23Y | 3.28 |
| 24 | 2 | 7.78 | 2.9Y | 2.8 | 49 | 3 | 8.0 | 2.21Y | 3.32 | 74 | 2 | 7.75 | 2.6Y | 3.5 |
| 25 | 2 | 7.75 | 3.15Y | 3.2 | 50 | 3 | 8.0 | 1.72Y | 3.32 | 75 | 2 | 7.75 | 1.0Y | 3.5 |

According to the teachings program, the student will be asked questions relating to these characteristics of hue, value, and chroma, however in terms of different degrees of colors, instead of hues, different degrees of "lightness", instead of values, and different degrees of "saturation", instead of chromas. To indicate to him what these terms mean, the student will be provided with a master definition sheet which indicates to him the type of characteristic difference he is looking for. For example: he may be told that sample 44 is a different color than sample 65. (It will be seen from the preceding table that these two samples have substantially the same value, 7.75, and chroma, 3.33 but differ in their hue by a perceptible amount, 0.37Y as compared to 3.27Y.)

(e) Sample 61?Sample A is selected identical to sample 43 in this test, and it will be seen that each sample occupies the second line in the array of FIG. 1, where their hue changes from left to right.

2. Question: Sample A is the same color as, but is more saturated than: (a) Sample 5; (b) Sample 20; (c) Sample 30; (d) Sample 55; (e) Sample 56?Sample A is selected identical to sample 75, and substantially corresponds in color to sample 20, 1.0Y as compared to 1.13Y, but is more saturated than sample 20, 3.5 as compared to 3.17. Therefore, the correct answer is (b).

3. Question: Which is correct: (a) Sample A is lighter than sample B; (b) Sample A is darker than sample B; (c) Sample A is a different color than sample B; (d) Sample A is more saturated than sample B; (e) Sample A is less saturated than sample B; (f) Sample A matches sample B?In one test, samples 54 and 57 were selected, to yield the correct answer that sample B was darker than sample A (value 8.0 as compared to value 7.75, substantially identical hues and chromas). In a second test, samples 7 and 17 were selected, to yield an answer that sample A was more saturated than sample B (chroma 3.5 as compared to chroma 2.8, values and hues being identical). In a third test, samples 2 and 62 were selected, with the correct answer then being that they are of different color (hue of .50Y as compared to hue of 3.45Y, substantially identical values and chromas).

4. Question: Sample A is the same as: (a) Sample 44; (b) Sample 45; (c) Sample 47; (d) Sample 58; (e) Sample 60?Sample A is selected identical to sample 58, and differs from each of the other samples by at least one discernible value, hue, or chroma characteristic.

5. Question: Samples 2 and 5 are different from Sample 18 because: (a) They are lighter; (b) They are darker; (c) They are of a different color; (d) They are more saturated; (e) They are less saturated?From the previous table, it will be seen that the correct answer is "b" because, although there exists some difference amongst all three samples in value, hue, and chroma, only the difference in value is discernible to the human eye.

6. Question: The proper order of samples 15, 30, 35, 46, 66 is: (a) 35, 30, 66, 15, 46; (b) 46, 15, 66, 30, 35; (c) 30, 35, 46, 15, 66; (d) 15, 46, 30, 66, 35; (e) 66, 35, 46, 30, 15?The answer, here, is "d", 15, 46, 30, 66, 35, which shows the same value and hue of the array of FIG. 2, but the increasing chroma levels of its Column "C".

7. Question: Sample A is the same as: (a) Sample 10; (b) Sample 43; (c) Sample 51; (d) Sample 63; (e) Sample 73?Sample A is selected identical to sample 10, and while it has the same value as all other samples, it has at least a differing hue and/or chroma than the other samples.

8. Question: Sample 71 belongs between: (a) Samples 1 and 72; (b) Samples 32 and 72; (c) Samples 31 and 32; (d) Before Sample 1; (e) After Sample 31?The correct answer is "c", between samples 31 and 32 since, while all samples have the same value and chroma, sample 71 has a color between samples 31 and 32, as shown in line 5 of FIG. 1.

9. Question: Sample 65 has the same lightness level as: (a) Sample 4; (b) Sample 11; (c) Sample 22; (d) Sample 29?From the foregoing table, it will be seen that the correct answer is "b", sample 4, where the slight difference in value, 7.77 as compared to 7.75 is imperceptible, and where only these two samples are included in the FIG. 2 array.

10. Question: Sample A is the same as: (a) Sample 6; (b) Sample 14; (c) Sample 20; (d) Sample 36; (e) Sample 45?Sample A is selected identical to sample 20, and although it has the same lightness as all other samples and only an imperceptible color difference from Sample 6, its chroma level differentiates it from this, as well as from all the other, samples. It will thus be seen from the foregoing questions — and from the tests within Question 3 — that 3 questions are primarily concerned with analyses of hue (color), 3 are concerned with value (lightness), 3 are concerned with chroma (saturation), and 3 are concerned with matching samples. Besides being readily apparent that this is an arbitrary number of questions of arbitrarily selected samples, it will be appreciated that the completion of this test would take of the order of 10–15 minutes, and that varied training could be provided merely by changing the samples which apply to any one question.

Testing has shown that students taking a course utilizing samples defined in this manner have exhibited much greater discrimination between colors than before the training program began. Not only did they become aware of slight differences in color, lightness and saturation, but they became far more cognizant of when colors matched. With this training, an improved dental shade guide then becomes not only a possibility but a practicability, in that superior matching results would not only be desirable but could be more easily attained.

While there has been described what is considered to be a preferred embodiment of the present invention of selecting color samples of defined hue, value and chroma characteristics for use in a test program to improve color discrimination, it will be readily apparent that changes can be made by those skilled in the art without departing from the teachings herein. Thus, while a 5x5 matrix array is shown in the drawing, other arrays could be used as well, depending upon the number of samples that were desired for any test program. It will similarly be noted that while the present invention is particularly attractive for use with the dental profession, where color characteristics are required to be closely matched, the teaching program described could also be used in other areas as well, where similar ability to distinguish between color shades would be desirable. For that reason, the scope of this invention should be interpreted in light of the claims appended hereto.

I claim:

1. Color discrimination test apparatus for teaching, training and educating in the dental matching of teeth, comprising: a plurality of color samples, wherein each of which is identified by a given hue, value and chroma level characteristic on the Munsell scale of color matching, wherein individual ones of which have no more than two of these identifying characteristics substantially identical, wherein the hue of each of said plurality of color samples falls within the range from approximately 8.0 yellow-red to approximately 4.0 yellow on said Munsell color matching scale, wherein the value of each of said plurality of color samples falls within the range 7.5 to 8.0 on said Munsell scale, wherein the chroma of each of said plurality of color samples falls within the range 2.5 to 4.0 on said color matching scale and wherein such differences as exist between individual samples with respect to their hues, values and chromas exceed 0.5, 0.1 and 0.2, respectively, on said scale.

2. The apparatus of claim 1 wherein individual ones of said plurality of color samples have at least one, but not more than two, of said identifying characteristics substantially identical.

3. A method of teaching color discriminations between and matchings of dental teeth, comprising the steps of selecting a plurality of color samples, each of which is identified by a given hue, value and chroma level characteristic on the Munsell scale of color matching, individual ones of which have no more than two of these identifying characteristics substantially equal, wherein the hue of each of said plurality of color samples falls within the range from approximately 8.0 yellow-red to approximately 4.0 yellow on said Munsell color matching scale, wherein the value of each of said plurality of color samples falls within the range 7.5 to 8.0 on said Munsell scale, wherein the chroma of each of said plurality of color samples falls within the range 2.5 to 4.0 on said color matching scale and wherein such differences as exist between individual samples with respect to their hues, values and chromas exceed 0.5, 0.1 and 0.2, respectively, on said scale, and comparing individual color samples, one against another in a prescribed manner, to determine differences in hues, values and chromas.

* * * * *